United States Patent [19]
Fletcher et al.

[11] 3,945,801
[45] Mar. 23, 1976

[54] INDICATOR PROVIDING CONTINUOUS INDICATION OF THE PRESENCE OF A SPECIFIC POLLUTANT IN AIR

[75] Inventors: James C. Fletcher, Administrator of the National Aeronautics and Space Administration, with respect to an invention of; Charles G. Miller, Pasadena; Ralph E. Bartera, La Canada, both of Calif.

[73] Assignee: The United States of America as represented by the United States National Aeronautics and Space Administration Office of General Counsel Code-GP, Washington, D.C.

[22] Filed: Nov. 7, 1974

[21] Appl. No.: 521,817

[52] U.S. Cl................. 23/254 E; 356/37; 250/574
[51] Int. Cl.² ............... G01N 1/22; G01N 21/26
[58] Field of Search........... 23/254 E, 254 R, 255 E, 23/255 R, 232 R, 232 C, 232 E; 356/37, 103, 104; 250/574, 222 PC; 73/28; 324/71 CP

[56] References Cited
UNITED STATES PATENTS

| | | |
|---|---|---|
| 2,431,899 | 12/1947 | Wolf et al. .................. 23/254 E X |
| 2,684,008 | 7/1954 | Vonnegut ............................ 356/37 |
| 3,094,392 | 6/1963 | Skala............................. 23/254 R X |
| 3,578,410 | 5/1971 | Van Luik, Jr..................... 23/232 R |

Primary Examiner—Robert M. Reese
Attorney, Agent, or Firm—Monte F. Mott; John R. Manning; Wilfred Grifka

[57] ABSTRACT

A continuous HCl in-air indicator consists of a tube-like element with an inlet end through which a continuous stream of air, containing HCl, enters. The air flows downstream from the inlet end and exits the element's outlet end. Positioned between the element's inlet and outlet ends are first and second spaced apart photoelectric units, which are preferably positioned adjacent the inlet and outlet ends, respectively. Ammonia gas is injected into the air, flowing through the element, at a position between the two photoelectric units. The ammonia gas reacts with the HCl in the air to form ammonium chloride particles. The difference between the outputs of the two photoelectric units is an indication of the amount of HCl in the air stream.

3 Claims, 2 Drawing Figures

INDICATOR PROVIDING CONTINUOUS INDICATION OF THE PRESENCE OF A SPECIFIC POLLUTANT IN AIR

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention:

The present invention generally relates to a device for indicating the presence of a specific pollutant, present among others in air and, more particularly, to a device for continuously indicating the presence of such a pollutant in a stream of air.

2. Description of the Prior Art:

One of the pollutants released into the atmosphere by rocket boosting of satellites into orbit is hydrogen chloride (HCl) gas, which is hygroscopic. The gas seeks out water in the form of vapor in the booster effluent and in the atmosphere to form mist droplets of hydrochloric acid solution which is highly corrosive. As is appreciated, the hydrochloric acid solution is actually HCl dissolved in water. For various reasons, it is necessary to determine the concentration of the HCl in the atmosphere, i.e., the air over an area extending several miles from the launch site at various altitudes. There are other situations in which it is desirable or necessary to determine the presence of other specific pollutants in air. Thus, a need exists for a simple, yet reliable, device for indicating the amount of a specific pollutant in the air.

OBJECTS AND SUMMARY OF THE INVENTION

It is a primary object of the present invention to provide a device which can receive a continuous stream of air containing various pollutants to provide an indication of the amount of a specific one of the pollutants in the air.

Another object of the present invention is to provide a relatively simple device capable of providing a continuous indication of the HCl content in the atmosphere, sampled by the device.

A further object of the invention is to provide a simple device capable of being flown through an atmosphere containing various pollutants to provide a continuous indication of the quantity of a specific one of the pollutants in the atmosphere.

The invention will be described in connection with an embodiment in which the specific pollutant to be detected is assumed to be HCl gas and/or droplets of hydrochloric acid solution. These and other objects of the invention are achieved by providing a device through which a stream of contaminated air passes continuously at a known flow rate. The air is assumed to contain various pollutants including HCl gas and/or droplets of hydrochloric acid solution. The particle content of the air is measured photoelectrically at a first location, by passing the polluted air through a first photoelectric unit. Following the first location downstream, a small jet of ammonia ($NH_3$) gas is introduced into the air stream. The $NH_3$ reacts with the HCl in the droplets of the hydrochloric acid solution or with the HCl gas and forms ammonium chloride particles which add to the particulate content of the air stream. The light transmission through air with ammonium chloride particles differs from that of air with droplets of hydrochloric acid solution or HCl gas. The air stream is then measured again photoelectrically by a second photoelectric unit at a second station, downstream from the location where the $NH_3$ is introduced and whereat the ammonium chloride particles are formed. The difference between the two photoelectric outputs is an indication of the conversion of the HCl into ammonium chloride and thus an indication of the amount of hydrogen chloride originally present in the air stream at the particular sample-taking location.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
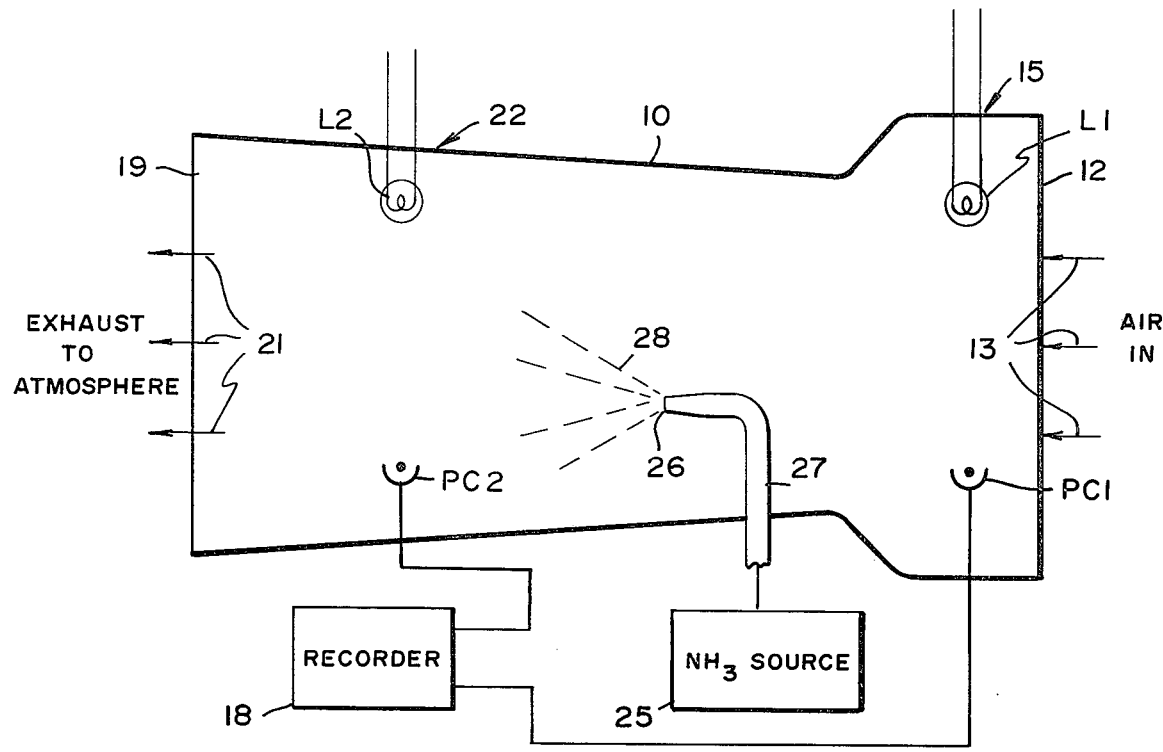
FIG. 1 is a cross sectional view of one embodiment of the invention.

In FIG. 1, numeral 10 designates a tube-like element with an inlet end 12 through which air, represented by arrows 13, is assumed to enter as a continuous stream at a known rate. The air 13 is assumed to contain pollutant particles including HCl. The HCl may be in gaseous form or in the form of droplets of hydrochloric acid solution, i.e., HCl dissolved in water. Downstream from the inlet end 12, a first photoelectric unit 15 is located. It consists of a light source, such as a bulb L1, and a light sensitive device such as a photocell PC1 which is located diametrically opposite the bulb L1. The output of the PC1, which is supplied to a recorder 18 as one input, is directly related to the light provided by bulb L1 and the light transmission through the polluted air which includes the HCl, and which passes between L1 and PC1.

The tube-like element 10 defines an outlet end 19 through which the air with any contaminants therein exits and is exhausted to the surrounding atmosphere. The exhausted air is represented by arrows 21. Adjacent the outlet end a second photoelectric unit 22 is located. It, like unit 15, includes a light source, such as a bulb L2, and a photocell PC2, located diametrically opposite thereto. The output of PC2 is provided to recorder 18 as a second input.

For explanatory purposes, it is assumed that the light provided by each of the bulbs L1 and L2 is the same and that the sensitivities of the two photocells PC1 and PC2 are the same. It should thus be appreciated that if the particles in the air are not modified in the element 10, the two photocells PC1 and PC2 would provide identical outputs, since the light transmission through the air with the original contaminants passing through unit 15 would be the same as that of the air passing through unit 22.

In accordance with the present invention the device includes a source of ammonia ($NH_3$) gas 25 from which a jet of ammonia is injected into the air stream in element 10 through a small opening 26 of a conduit 27, which extends from the source 25. The $NH_3$ jet is represented by dashed lines 28. The $NH_3$, introduced into the stream of air in element 10, reacts with the HCl in the air, whether the HCl is in gas form or is dissolved in water in the form of droplets of hydrochloric acid solution. The reaction of the $NH_3$ with the HCl produces ammonium chloride particles, which add to the particulate content of the air stream, and flow with the air through unit 22, i.e., between the bulb L2 and PC2 and are then exhausted with the air steam through outlet 19. Thus, the HCl pollutant in the entering air stream 13 is converted into a different pollutant, i.e., ammonium chloride as the air passes through element 10.

Ignoring the effect on light transmission of other pollutants in the air which are not of interest and are not affected by $NH_3$, the light transmission characteristic of air with HCl gas or droplets of hydrochloric acid droplets differs from that of the air with ammonium chloride particles. Consequently, even with bulbs L1 and L2 being identical and PC1 and PC2 having the same sensitivity, since air with HCl passes through the first unit 15 and air with ammonium chloride particles passes through the second unit 22, the two photocells will produce different rather than identical outputs. The difference between their outputs, which are supplied to recorder 18, is an indication of the conversion of the HCl into ammonium chloride and thus is an indication of the amount of HCl originally present in the air stream entering the element 10 at the particular sample-taking location.

Since the air flow of air in element 10 and the injection of the ammonia may be continuous the device may be used to provide a continuous indication of the HCl in the continuously sampled air. From the foregoing, it should thus be apparent that in accordance with the present invention, the particular pollutant of interest in the air stream is detected by converting it into a different type of pollutant which has different light transmission properties. The conversion is done as the air flows continuously through the device. The amount of the pollutant of interest is indicated by the difference between the outputs of the two photocells as compared with their outputs under initial or calibration conditions, i.e., when the same matter passes through both units.

Figure 2:
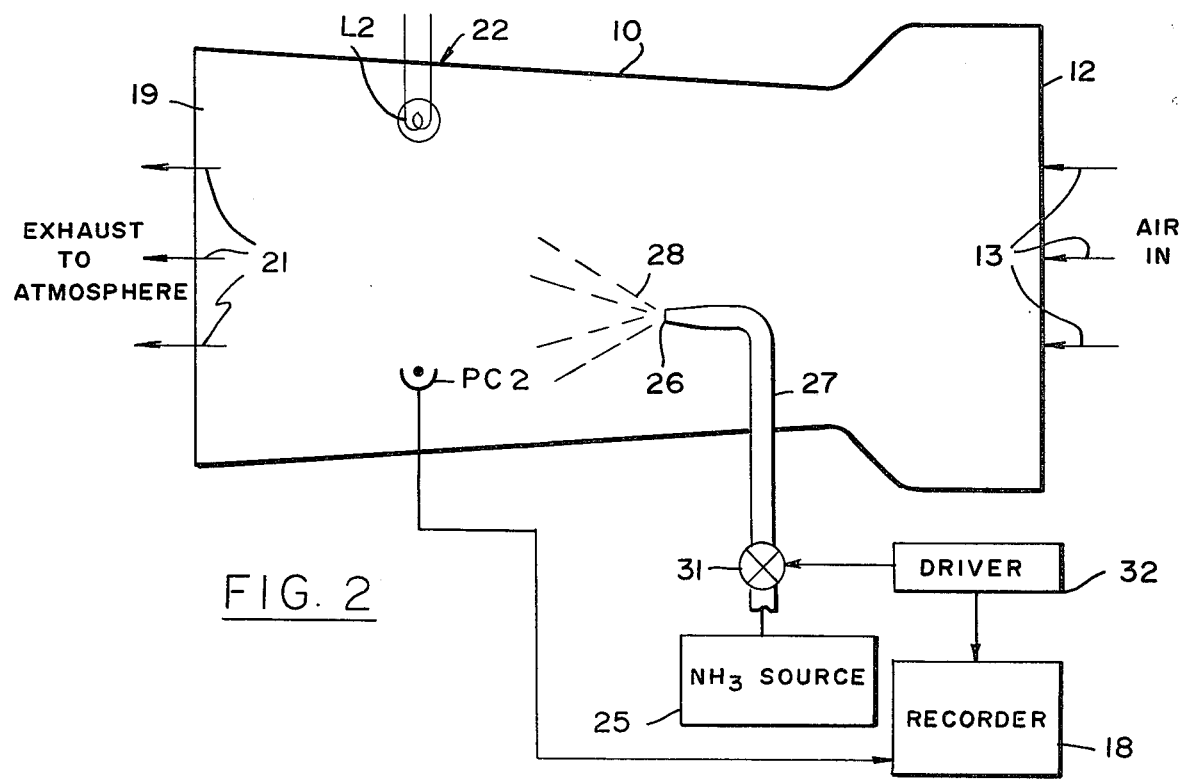
FIG. 2 is a cross sectional view of another embodiment of the invention.

In the embodiment shown in FIG. 1, the device is shown with two photoelectric units 15 and 22. If desired, the device may include only unit 22 and means provided to operate the $NH_3$ jet stream in a pulsed mode. Such an arrangement is shown in FIG. 2. Therein, a valve 31 is shown in conduit 27. The valve is assumed to be driven between open and closed positions by a driver 32. In the open position, $NH_3$ flows from source 25 through the valve and therefore a jet of $NH_3$ is injected into the air stream. In the closed position $NH_3$ is prevented from reaching the air stream. The driver may be connected to the recorder to indicate the valve position.

When $NH_3$ is not injected, air with the unmodified HCl passes through unit 22 and the output of PC2 is of one level. Then, when the valve is opened and $NH_3$ is injected into the stream the ammonium chloride particles are formed and the PC2 output changes to another level. Thus, the difference between the two levels of the PC output is indicative of the amount of HCl in the air entering element 10. In this embodiment it is assumed that the amount of HCl does not vary between the sample or quantity of air in which the HCl is not converted into ammonium chloride particles, and the succeeding sample of air into which the $NH_3$ is injected to react with the HCl and convert it into ammonium chloride.

In the embodiment of FIG. 1, a continuous indication of the HCl in the continuous stream of air is provided. However, in the FIG. 2 embodiment the indication is of the HCl in alternate air samples, spaced apart by air samples whose HCl content is used as a reference. By increasing the rate of valve switching the indication is for all practical purposes of the HCl in a continuous air stream.

Although the invention was conceived in connection with developing a continuous HCl in-air indicator and was described in connection with indicating the amount of HCl in sampled air, it is not intended to be limited thereto. Indeed the device with the one or two photoelectric units may be used to indicate the amount of any air pollutant which has a given light transmission property and which can react with a known compound or compounds to form particles with different light transmission properties. For example, the presence in air of various pollutants containing sulphur, such as $H_2S$ can be detected by injecting into the air stream any one of several different lead salts, rather than $NH_3$. In such an application, the lead would combine with the sulphur to form lead sulfide (PbS) particles which are black, thereby affecting the light transmission properties. The lead salts such as lead nitrate or lead acetate would only affect the sulphur-containing pollutants, whose presence in the air would be indicated by the difference in the outputs of the two photocells or by the different successive outputs of the same cell (FIG. 2 embodiment).

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A device for indicating the amount of a specific pollutant present among various pollutants in a stream of air comprising:

a single elongated hollow tube-like element having a first open end and a second open end, diametrically opposite said first open end, said first open end defining an inlet end through which a continuous stream of air containing various pollutants, including a specific pollutant, is adapted to enter and flow continuously downstream along the entire length of said element and exit through said second end defining an outlet end of said element;

a first photoelectric unit positioned upstream from said outlet end and including a first light source and first light sensitive means, positioned directly in the path of light from said source, for receiving the light directly directed thereto from said first light source, said first light sensitive means being spaced apart from said first light source in a direction perpendicular to the element's length direction along which the air flows from said inlet end to said outlet end, so that at least a portion of the air flowing through said element passes between said first light source and said first light sensitive means, the latter providing an output which is a function of the light directed thereto from said first light source and the light transmission characteristics of the air with the various pollutants including said specific pollutant contained therein; and source means for injecting selected matter into the air flowing through said element at a location upstream from said first photoelectric unit, whereby the selected matter reacts inside said element with the specific pollutant in said air to form compound particles carried by said air past said first photoelectric unit, the air with said compound particles having light transmission characteristics which differ from those of the air with the specific pollutant therein.

2. The device as described in claim 1 further including a second photoelectric unit positioned upstream from the location whereat the selected matter is injected into the air in said element, said second unit including a second light source and a second light sensitive means spaced apart from said second light source directly in the path of the light from said second light source and in a direction perpendicular to the element's length direction along which the air flows from said inlet end to said outlet end, so that the air containing various pollutants including said specific pollutant and entering said element, passes between said second light source and said second light sensitive means, the latter providing an output which is a function of the illumination of the second light sensitive means by the light transmitted by said second light source directly to said second light sensitive means through the air containing said pollutants including said specific pollutant and flowing therebetween, said source means continuously injecting said selected matter into said air which passed said second unit to convert substantially all the specific pollutant in said air into said compound particles, which pass together with the air past said first unit, and means for receiving the outputs of said first and second light sensitive means.

3. A device for measuring the amount of a selected first compound present in a continuous stream of a carrier gas essentially consisting of:
a single elongated hollow tube-like element having a first open end and a second diametrically opposite second open end, the distance between said open ends defining the length of said element, said first open end defining an inlet end through which a continuous stream of a carrier gas containing said first compound is adapted to flow continuously downstream along the entire length of said element and exit through said second open end, which defines an outlet end of said element;

a single photoelectric unit positioned upstream from said outlet end and including a single light source and a single light sensitive means, spaced apart from said single light source in a direction which is substantially perpendicular to the element's length direction, along which the carrier gas flows from said inlet end to said outlet end, so that at least a portion of said carrier gas passes between said single light source and said single light sensitive means, the latter being positioned directly in the path of light from said light source, for providing an output which is a function of light which is directly directed thereto from said single light source and the light transmission characteristics of the carrier gas and any compounds carried therein;

source means including an outlet nozzle in communication with said element for injecting discrete quantities of a selected second compound into said element, through which said carrier gas with said selected compound flow, during discrete intervals, spaced apart by periods during which said selected second compound is not injected into said element, said first and second compounds reacting in said element to form therein particles of a selected third compound, which are carried by said carrier gas past said single photoelectric unit, the light transmission characteristics of said carrier gas with particles of said third compound being different from the light transmission characteristics of said carrier gas with said first compound; and output means coupled to said single light sensitive means for sensing the output thereof.

* * * * *